United States Patent [19]

Lewis et al.

[11] Patent Number: 5,177,872
[45] Date of Patent: Jan. 12, 1993

[54] METHOD AND APPARATUS FOR MONITORING PHYSICAL POSITIONING OF A USER

[75] Inventors: Russell F. Lewis, Dallas; Robert J. Gove, Plano; Dale A. Cone, Garland, all of Tex.

[73] Assignee: Texas Instruments Incorporated, Dallas, Tex.

[21] Appl. No.: 593,823

[22] Filed: Oct. 5, 1990

[51] Int. Cl.⁵ .................................... G01C 9/06
[52] U.S. Cl. ....................................... 33/366
[58] Field of Search ............... 33/366, 377, 312, 313; 340/686, 689, 566; 250/573, 577, 231 R

[56] References Cited

U.S. PATENT DOCUMENTS

| | | | |
|---|---|---|---|
| 3,184,861 | 5/1965 | Conrad | 33/366 |
| 3,478,437 | 11/1969 | Cothran | 33/366 |
| 3,713,338 | 1/1973 | Kind | 73/293 |
| 4,154,000 | 5/1979 | Kramer | 33/366 |
| 4,779,353 | 10/1988 | Lopes et al. | 33/366 |
| 4,861,981 | 8/1989 | Winiger | 33/366 X |

FOREIGN PATENT DOCUMENTS 920617  1/1947  France .................... 33/366

Primary Examiner—Harry N. Haroian
Attorney, Agent, or Firm—L. Joy Griebenow; Richard L. Donaldson; William E. Hiller

[57] ABSTRACT

There is disclosed a device and method for providing signals representative of the positional altitude of a user. The device is responsive to hand or head movements to move a dampened substance contained within a confined tube past one or more sensors. Light passing through the tube is interrupted by the movement of the dampened substance which can be a liquid or a solid object within a viscous liquid.

14 Claims, 2 Drawing Sheets

METHOD AND APPARATUS FOR MONITORING PHYSICAL POSITIONING OF A USER

TECHNICAL FIELD OF THE INVENTION

This invention relates to motion sensors and more particularly to a method and apparatus for a sensor which is portable, light weight and adaptable to be worn or hand held by a user.

CROSS REFERENCE TO RELATED APPLICATIONS

The following patent applications are cross-referenced to one another, and all have been assigned to Texas Instruments Incorporated. These applications have been concurrently filed and are hereby incorporated in this patent application by reference.

| Ser. No. | Filed | Title |
| --- | --- | --- |
| 593,190 | 10/05/90 | Method and Apparatus for Providing a Portable Visual Display |
| 593,823 | 10/05/90 | Method and Apparatus for Monitoring Physical Positioning of a User |
| 593,702 | 10/05/90 | Method and Apparatus for Presentation of On-Line Directional Sound |

BACKGROUND OF THE INVENTION

The relative position and altitude of a person or object is important to monitor for many reasons. For example, in an artificial reality system, such as that disclosed in the above-identified copending patent application entitled "Method and Apparatus for Providing a Portable Visual Display," it is necessary to continually determine the direction a viewer is facing, the viewer's motion and the speed of the viewer's movements.

In the past, such measurements have been made using expensive, typically bulky, equipment.

In portable artificial reality systems, light weight and economy are mandatory since, in one embodiment, the viewer wears the directional sensor on a helmet, and in other embodiments carries the directional sensors in his/her hand.

Typically, such sensors are flux gate compasses, cameras, radio wave detectors and sensors, spring loaded acceleration devices, and other sophisticated devices, usually relying on magnetic flux detection or visual imaging. Also, usually such sensors require calibration each time a user begins a session using the device.

Thus, there is a need in the art for a positional sensor which is self contained, light weight and economical to manufacture.

There is a further need in the art for such a sensor which allows for positional determination and velocity calculations while still remaining portable and reliable.

There is still a further need in the art for such a sensor which requires no calibration upon initial use and which is without mechanical moving parts.

SUMMARY OF THE INVENTION

A method and device have been devised which allows for the monitoring of a tube containing a liquid, or alternatively, a solid object, by a light sensing device such as a CCD. In operation, a linear CCD array is positioned to detect light passing through the tube. As the tube is tilted from the horizontal, gravity will cause the surface of the liquid (or solid object) to move (rise or fall) with respect to the CCD sensor array, blocking the light and causing signals to be generated dependent upon the relative position of the liquid within the tube.

In one embodiment, it is a trapped air bubble within the liquid which causes a light change to occur with respect to each CCD mounted to the tube. The number of CCDs "on" or "off" at any given instant of time is integrated over a period of time to provide an indication of motion direction and speed. The CCD array can be integrally packaged with the tube or could be detachably mounted. This device is economical to manufacture, light in weight and without mechanical moving parts.

The processing, based upon the speed with which the signals from the individual CCD sensors change, calculates the positional movement of the user. There can be one such sensor for each plane of possible movement so that a system can have three, or more, such sensors for precise motion and speed determination over a wide range of possible motion.

In one embodiment, two such devices can be used to define three planes of motion. This is accomplished by measuring the highest point of the liquid and the lowest point and then calculating the angle or tilt between these points. Thus, one device can provide two dimensions.

It is thus one technical advantage of this invention to provide a level measuring device which is portable, light weight, economical, and without mechanical moving parts and which is capable of use without initial calibration.

It is a further technical advantage of this invention that the fluid level within a confined enclosure can be monitored to determine the direction of change and the rate of change.

BRIEF DESCRIPTION OF THE DRAWINGS

A more complete understanding of the present invention may be acquired by referring to the detailed description and claims when considered in connection with the accompanying drawings in which like reference numbers indicate like features wherein:

DETAILED DESCRIPTION OF THE INVENTION

Figure 1:
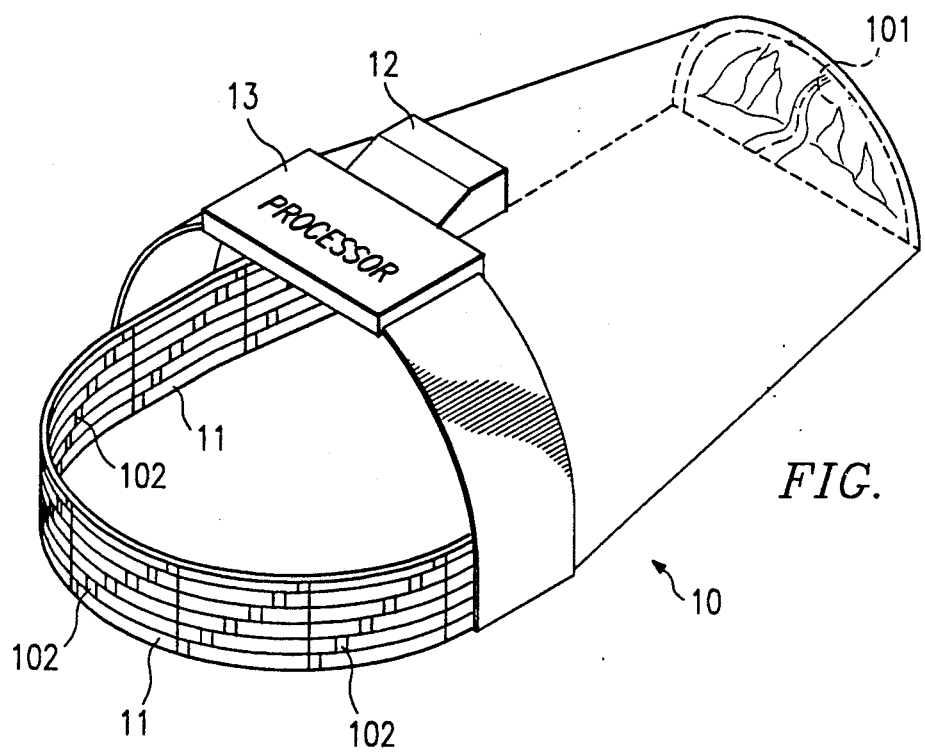
FIG. 1 is a helmet mounted virtual reality device with the speaker elements exposed.

FIG. 1 depicts a portable virtual reality system 10 worn by an individual on his or her head. System 10 consists of a color liquid display screen 101, an array of piezoelectric film elements 102, a position-orientation sensor 12 and a processor 13.

Processor 13 generates a visual picture according to helmet 10 orientation information from position-orientation sensor 12 and on board software. Processor 13 creates a three dimensional environment and projects a view of it on screen 101. As the user moves his/her head and, hence, helmet 10, processor 13 changes the image on screen 13 to mimic the view the user would perceive if he/she were actually in the three dimensional environment. Similarly, if the user walks or runs to a new location, processor 13 changes the image on screen 101 as if the user walked or ran the same distance and direction in the three dimensional environment.

Note that while screen 101 is a color liquid crystal display, it can be any type of display and can, for example, be positioned close to a user's eyes with a short focal length.

Processor 13 also generates a sound field through piezoelectric elements 102 of sound band 11. Individual elements 102 are separately driven by processor 13. The processor selectively powers piezoelectric film elements 102 on an individual basis to create a directional sound field. By doing so, the processor can create the illusion of a moving sound source and of a stationary sound source when the user's head or body moves. The sound source would be stationary, i.e., the same sound would continue to come from the same elements when the user stops moving. The sound elements can be small chips or elongated bands, each driven by a separate signal from the processor.

Figure 2:
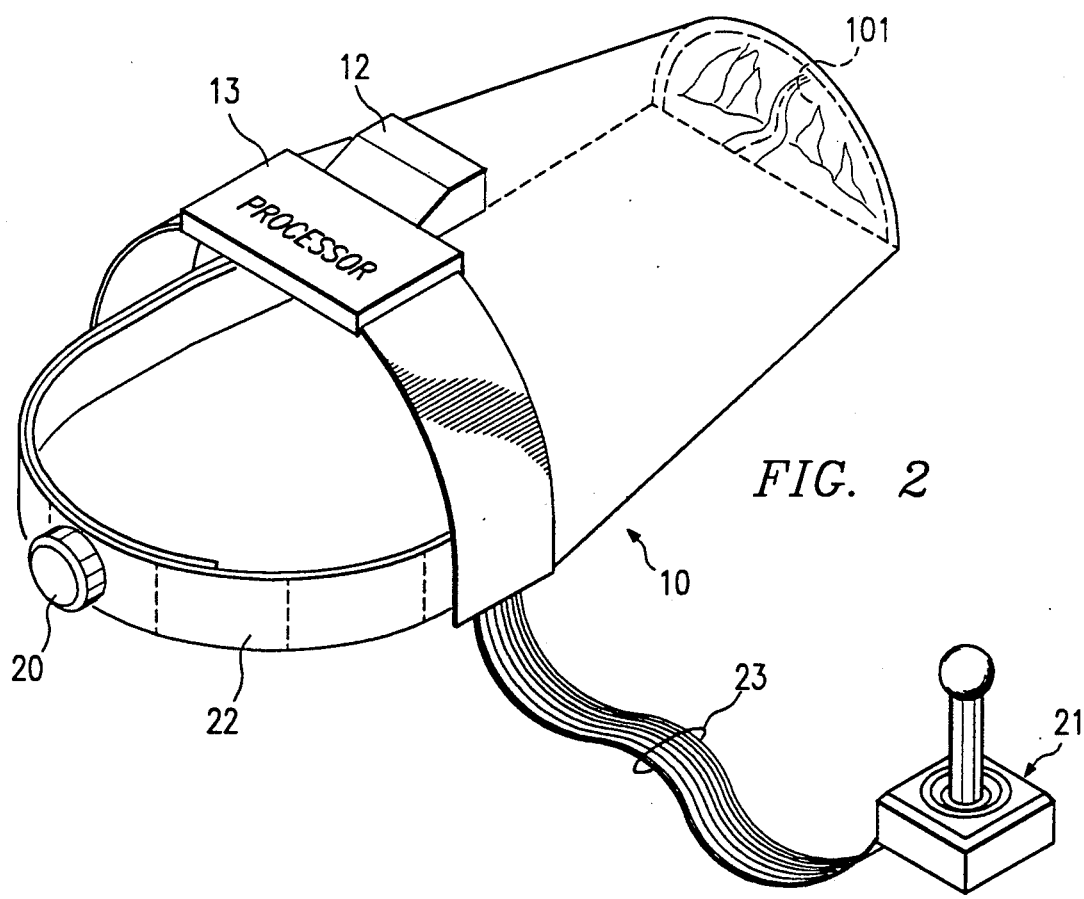
FIG. 2 is also a helmet mounted virtual reality device.

FIG. 2 shows a system in which the user, using control 21, manually changes the presented image or manually creates a change in direction or speed with respect to the created environment. Band 22 contains elements 102 and can be adjusted via tightening mechanism 20, which can also be a volume control for the elements.

Figure 3:
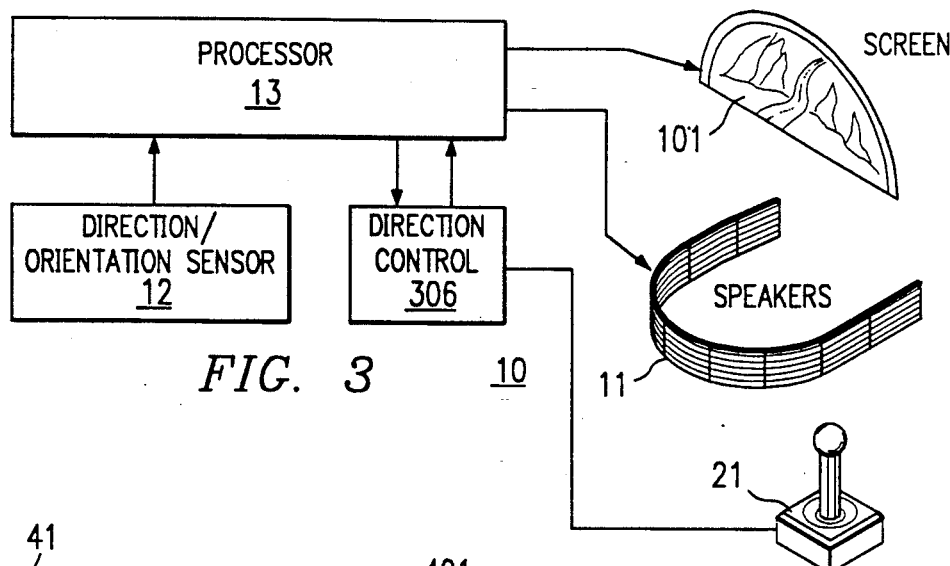
FIG. 3 is a schematic representation of a simulated reality system.

FIG. 3 schematically depicts processor 13, screen 101, speaker elements 11, joystick 21, position-orientation sensor 12 and direction control module 306. Processor 13 takes graphic information stored in a data base and generates images that are displayed on screen 101. Processor 13 also generates sound projected from piezoelectric film segments 102. Processor 13 could be a single processor or multiple processors such as a graphics processor from the TMS340 series and a digital signal processor from the TMS320 series, all available from Texas Instruments Incorporated. The '340 generates images shown on screen 101 and the '320 generates sound on element band 11. Connected to processor 13 is a position-orientation sensor 12. Position-orientation sensor 12 senses the direction that the user is looking. A flux gate compass (not shown) may also be linked to processor 13 to provide absolute north-south orientation information. Direction control block 306 provides processor 13 with information indicating the user's location and view within the three dimensional environment. Direction control block 306 receives user orientation information from position sensor 12 through processor 13 and from the user directly through joystick 21. Direction control block 306 can determine the user's position within the three dimensional environment by mathematically integrating the instantaneous orientation information from position-orientation sensor 12.

Figures 4A, 4B, 4C:
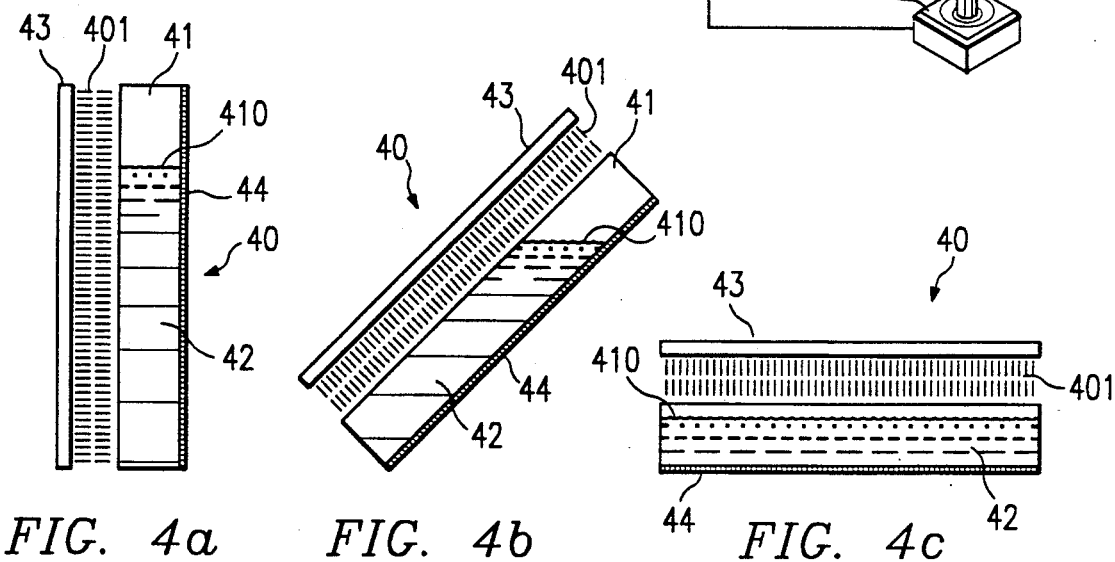
FIGS. 4a, 4b and 4c depict a CCD position-orientation sensor in various orientations.

FIGS. 4a, b and c depict an element in an embodiment of a position and orientation sensor 12. Container 40 is fluid filled and has light source 43 (or other source of electronic signals such as infrared or microwave) on one side and CCD 44 ("charge coupled device") or other electronic signal detectors on the other. CCD 44 is able to sense where light 401 impinges on it from source 43 and when light is blocked by fluid 42. FIGS. 4b and 4c depict different orientations of assembly 40 and hence depict different levels of fluid in device 40.

In FIG. 4b as assembly 40 is tilted down, a larger area of CCD 44 is blocked by fluid 42, allowing less light 401 to strike CCD 44. The amount of light impacting CCD 44 can be detected, for example, by using an array of individual CCD (or other detectors) devices, and monitoring, perhaps on a digital basis, the light level. When horizontal, no light gets through to CCD 44. In FIG. 4c fluid completely covers CCD 44.

Figure 5:
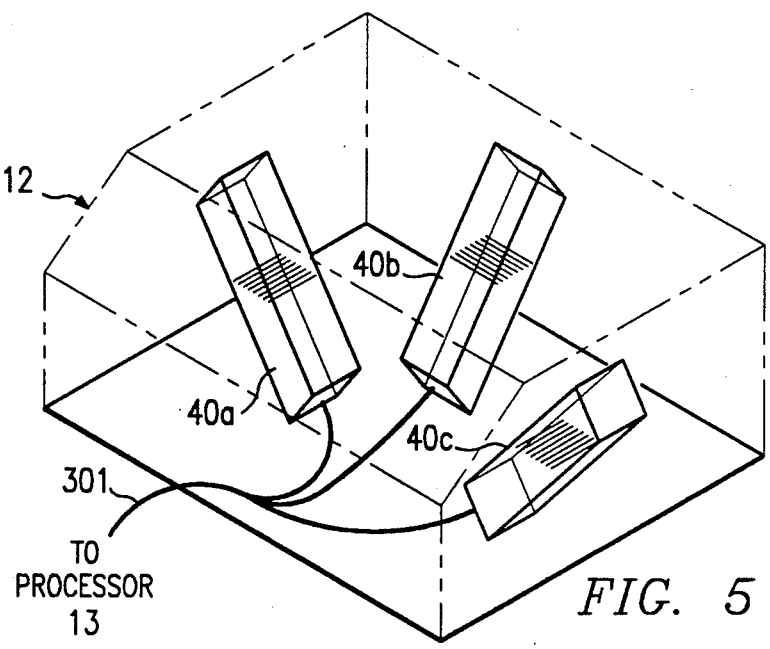
FIG. 5 shows a three-dimensional position-orientation sensor.

In FIG. 5 a number of CCD assemblies 40 can be combined to indicate the tilt in different axes. Three assemblies, 40a, 40b and 40c are aligned along mutually orthogonal axes and encapsulated in direction sensor 12 to detect motion in three dimensions. The orientation information from assemblies 40a, 40b and 40c is transmitted through cable 301 to processor 13. The CCD assemblies can also provide information on the motion and position of sensor 12 by examining the output of CCD device over time.

It is possible to use only two devices to obtain all three orientations by taking into account the slope of liquid within each device 40.

Although this description describes the invention with reference to the above specified embodiments, it is but one example, and the claims, not this description, limit the scope of the invention. Various modifications of the disclosed embodiment, as well as alternative embodiments of the invention, will become apparent to persons skilled in the art upon reference to the above description. Therefore, the appended claims will cover such modifications that fall within the true scope of the invention.

What is claimed is:

1. A motion detector, said motion detector comprising:
   a tube containing a liquid, said liquid having a surface area defining a plane, said surface area movable within said tube in response to the inclination of said tube such that said plane forms an angle with respect to said tube;
   an emitter for transmitting first signals and positioned on a first side of said tube;
   a sensor positioned on a second side opposite to said first side and operable to detect said first signals so that said first signals may be transmitted from said emitter to said sensor; wherein said liquid is operable to restrict the transmission of said first signals and wherein the amount of said first signals detected by said sensor is indicative of said angle between said surface area and said tube; and
   a processor connected to said sensor and operable to continously monitor changes in said angle, thereby measuring said motion.

2. The detector set forth in claim 1 wherein said sensor includes:
   a signal generator for providing discrete second signals indicative of the length of said surface area within said tube.

3. The detector set forth in claim 2 wherein said emitter emits light rays; and
   said signal generator includes a plurality of discrete light detectors, each said detector spaced apart along the length of said tube and adapted to provide said signals depending upon the changing magnitude of light rays detected.

4. The detector set forth in claim 3 wherein said discrete light detectors include CCD devices.

5. A motion sensor comprising:
   at least one emitter operable to emit a first signal;
   a defined space adjacent to said at least one emitter within which a fluid is free to flow in accordance with gravity, wherein said fluid restricts the propagation of said first signal, said fluid having a surface area defining a plane whereby said plane forms an angle with respect to said defined space;

a plurality of detectors abutting said defined space for continuously detecting said first signals and wherein the amount of first signals detected is indicative of said angle; and a processor connected to said plurality of detectors and operable to continously monitor said angle, thereby detecting said motion.

6. The motion sensor set forth in claim 5 further comprising:

a signal generating device connected to said plurality of detectors for providing second signals representative of the status of said detectors.

7. The sensor set forth in claim 5 wherein said first signal is light and said detectors are sensitive to light passing through said confined space as modified by said liquid moving within said space.

8. The sensor set forth in claim 7 wherein said detectors include a linear CCD array spaced along the longitudinal axis of said defined space.

9. The sensor set forth in claim 7 wherein said light is provided by a light source abutting said defined space.

10. A method of detecting motion comprising the steps of:

providing within a tiltable vessel having walls a liquid restrictive of the transmission of a first signal and having a surface area defining a plane, said surface area movable within said vessel in response to the tilting of said vessel thereby producing an angle between said surface area and said walls;

monitoring a relative amount of transmission of said first- signal thereby detecting said angle as it changes as said surface area moves within said vessel; and continuously monitoring said angle, thereby detecting motion of said tiltable vessel.

11. The method set forth in claim 10 wherein said monitoring step includes the step of:

providing discrete second signals indicative of the length of said surface area within said vessel.

12. The method set forth in claim 11 wherein said first signal is light rays; and said providing step includes the step of:

interrupting light from discrete light detectors, each said detector spaced apart along the length of said tube and adapted to provide said second signals depending upon the changing magnitude of light rays passing through said tube.

13. The method set forth in claim 12 wherein said discrete light detectors include a linear array of CCD devices.

14. The method set forth in claim 10 further comprising the step of sending said second signals to a remote device.

* * * * *